United States Patent
Ilgenfritz et al.

(10) Patent No.: US 12,017,367 B2
(45) Date of Patent: Jun. 25, 2024

(54) BARRIER SYSTEM WITH HANDLING DEVICE FOR AUTOMATED SAMPLING AND METHOD FOR AUTOMATED SAMPLING

(71) Applicant: Syntegon Technology GmbH, Waiblingen (DE)

(72) Inventors: Markus Ilgenfritz, Feuchtwangen (DE); Ulrich Krauß, Ilshofen (DE); Stefan Nagler, Unterschneidheim (DE); Samuel Stegmeier, Kreßberg (DE)

(73) Assignee: Syntegon Technology GmbH, Waiblingen (DE)

( * ) Notice: Subject to any disclaimer, the term of this patent is extended or adjusted under 35 U.S.C. 154(b) by 0 days.

(21) Appl. No.: 18/361,382

(22) Filed: Jul. 28, 2023

(65) Prior Publication Data
US 2024/0058967 A1 Feb. 22, 2024

(30) Foreign Application Priority Data
Aug. 16, 2022 (DE) .................... 10 2022 120 677.7

(51) Int. Cl.
| | | |
|---|---|---|
| *B25J 9/16* | (2006.01) | |
| *B25J 11/00* | (2006.01) | |
| *B25J 15/00* | (2006.01) | |
| *B25J 21/00* | (2006.01) | |

(52) U.S. Cl.
CPC .......... *B25J 9/1682* (2013.01); *B25J 9/1653* (2013.01); *B25J 11/005* (2013.01); *B25J 15/0028* (2013.01); *B25J 21/00* (2013.01)

(58) Field of Classification Search
CPC ...... B25J 9/1682; B25J 9/1653; B25J 11/005; B25J 15/0028; B25J 21/00
See application file for complete search history.

(56) References Cited

U.S. PATENT DOCUMENTS

| | | |
|---|---|---|
| 2004/0185521 A1 | 9/2004 | Yoshida et al. |
| 2022/0003796 A1 | 1/2022 | Ahlfors |
| 2022/0251488 A1 | 8/2022 | Metzger et al. |
| 2023/0029276 A1* | 1/2023 | Mcelligott ............... B25J 11/00 |

FOREIGN PATENT DOCUMENTS

| | | |
|---|---|---|
| CN | 111518689 A | 8/2020 |
| DE | 102020133609 A1 | 6/2022 |
| WO | 2013002268 A1 | 1/2013 |
| WO | 2014174455 A1 | 10/2014 |

OTHER PUBLICATIONS

Canadian Patent Office Action for Application No. 3,204,605 dated Aug. 24, 2023 (8 pages).

(Continued)

*Primary Examiner* — Basil T. Jos
(74) *Attorney, Agent, or Firm* — Michael Best & Friedrich LLP (57) ABSTRACT

A barrier system of a production plant, in particular a pharmaceutical production plant, with a closed or separate area in which a sterile environment is provided, wherein a handling device for automated sampling with a contact sample is arranged in the closed or separate area, as well as methods for automated sampling.

21 Claims, 11 Drawing Sheets

(56) References Cited

OTHER PUBLICATIONS

German Patent Office Action for Application No. 10 2022 120 677.7 dated Mar. 24, 2023 (10 pages with English translation).
German Patent Office Decision to Grant for Application No. 10 2022 120 677.7 dated May 2, 2023 (14 pages with English translation).
Kannan et al., "A systematic review with narrative synthesis on medical robots and laboratory automation in the control of the SARS-CoV-2, Ebola, and H1N1 (Swine Flu) viruses", Journal of Health and Social Sciences, 2020, vol. 5, No. 2, pp. 193-208.
Translation of European Patent Office Extended Search Report for Application No. 23182737.9 dated Jan. 15, 2024 (10 pages).

* cited by examiner

BARRIER SYSTEM WITH HANDLING DEVICE FOR AUTOMATED SAMPLING AND METHOD FOR AUTOMATED SAMPLING

BACKGROUND

For microbiological monitoring in e.g., a pharmaceutical production plant, Petri dishes and contact samples are often used. These are plastic dishes filled with nutrient medium (e.g., agar) and fitted with a lid. Petri dishes are used for monitoring the air, and contact samples are used for monitoring surfaces.

In order to enable sampling on surfaces, the contact samples are designed in such a way that the nutrient medium protrudes slightly over the edge of the plastic dish (referred to below as the bottom). The two microbiological samples (Petri dishes and contact samples) differ in size and shape, but both are usually supplied in stacks of 10, triple-sterile and packaged in tubular foil bags.

The bags containing the microbiological samples are brought into a pharmaceutical production plant for use, where they are unpacked via glove ports or automated. Finally, they are ready for monitoring, e.g., in a magazine.

As part of "good manufacturing practice" in pharmaceutical production plants, contact samples are usually taken after the end of production to pick up any microorganisms (such as fungi or bacteria) that may be present on surfaces and to subsequently hatch them in an incubator.

In currently known pharmaceutical production plants, this process is carried out manually by the operating personnel after the end of production. In a production plant with a barrier system, for example, which can be designed as an isolator, this is done by an operator who uses glove ports to access the plant. The operator removes an unused contact sample from, e.g., a magazine. The operator removes the lid from the sample and performs the sample collection by pressing the tray onto the surface to be tested. Afterwards, the operator puts the lid back on the tray and labels the contact sample (e.g., when the sample was taken and at which location in the plant). Usually, the sample is finally placed back into the magazine.

The documentation of the location where the sample was taken is of great importance, since the contact samples are also used to prove the effectiveness of disinfection and decontamination measures, such as the decontamination cycle with hydrogen peroxide ($H_2O_2$), in critical production areas. Only if it is documented without gaps and errors at which location which sample was taken, can e.g., batches be released or also blocked or decontamination and disinfection measures be improved in a targeted manner when microorganisms are detected by the incubation.

After the contact samples have been performed at all designated locations, the production plant can be opened, the magazine containing the microbiological samples can be removed, and the microbiological samples can be incubated in a laboratory.

It is possible to remove the microbiological samples from the production machine via, for example, an RTP transfer system with double doors (so-called rapid transfer ports, consisting of alpha ports and beta container), so that they do not have to be transported through a potentially non-sterile room. However, since the samples are closed by a lid, in practice they are usually removed from the plants with the doors open and taken to a laboratory.

The previous solutions have the disadvantage that sampling on surfaces requires an operator to intervene in the production plant via gloves. However, the glove ports represent a possible contamination risk for the machine and thus also for the product to be processed. Furthermore, there is a risk of contamination due to the gloves being worn when taking the sample and it is therefore wrongly assumed that the plant was contaminated during the preceding production. For this reason, it is desirable to dispense with glove ports in modern pharmaceutical production plants with barrier systems. This is referred to as a gloveless barrier system or "gloveless isolator". Without glove ports, however, sampling on surfaces by the operator is no longer possible. It is also not possible to open the doors before taking samples on the surfaces, as this could cause contamination of the plant from outside, which was not yet present during production.

Furthermore, the previous solutions (by means of an operator and glove port) for carrying out the contact samples have the disadvantage that they are not reproducible, since the sampling on critical surfaces is carried out by an operator, who does not always take the sample at exactly the same location and does not always press the contact tray against the surface with exactly the same force for the same time. The sampling conditions therefore vary from sample to sample.

Furthermore, there is a risk that errors may be made by the operator when documenting the location of the sampling and that it may not be possible to assign the individual samples to the sampling locations at a later date.

SUMMARY

The present invention is based on the task of improving the reliability of sampling on surfaces of pharmaceutical production plants.

The present invention enables fully automated and reproducible sampling on surfaces of pharmaceutical production plants without any intervention by the operating personnel. In classical plants with barrier systems with glove ports, the handling steps by the operator can be minimized with the invention, and the contact samples can be performed reproducibly and documented without errors.

The invention provides a barrier system for this purpose. This barrier system may in particular be an isolator. The barrier system is part of or provided for a production plant. The production plant is in particular a pharmaceutical production plant. The barrier system may also be a restricted access barrier system (RABS). RABS physically separate products and processes from the production environment and the user, thus ensuring a high level of product and operator protection. This is typically a protective enclosure with glass panels, with directional airflow prevailing in the separated area, but the separated area is not completely enclosed; air can flow downward (e.g., just above the tabletop) to the outside.

The barrier system can be closed with a closed area in which a sterile environment is provided. The barrier system can also be open (RABS) with a separated area that is not completely closed but in which a sterile environment is provided (the degree of sterility here is typically lower than in a system with a closed area, but in the following we will refer to a sterile environment in both cases).

According to the invention, it is now provided that a handling device and a contact sample holder are arranged in the closed or separated area. The contact sample holder is designed to provide at least one sample. The handling device is designed to automatically remove and open the provided contact sample from the contact sample holder and to reproducibly perform a sampling on a surface section in the closed or separated area. By reproducible is meant that the handling device is able to repeat a sampling process with the same sampling parameters, for example with the same pressure duration and the same pressure of the sample. The sampling parameters are in particular stored and/or can be read out. The handling device is designed to carry out the steps automatically, i.e., without the need for human intervention, e.g., by means of glove ports, or it can also be provided that the sampling is carried out without direct control, but within the framework of a predefined sequence. For example, a robot arm can be used. In particular, the handling device can take samples from several sampling locations.

A contact sample in the sense of the present invention comprises a bottom on which a nutrient medium, in particular agar, is arranged. In the initial state, the contact sample is closed with a lid.

Opening of the contact sample is done by removing the lid from the bottom of the contact sample.

Sampling is performed by contacting a location to be sampled with the nutrient medium of the contact sample. In particular, it is envisaged that the contact sample is aligned with the nutrient medium downwards and the bottom upwards before sampling (by means of the handling device) and is then moved onto the surface to be sampled, in particular with a movement perpendicular to the surface of the nutrient medium. In particular, the surface to be sampled is brought into contact with the nutrient medium at a predetermined pressure and/or for a predetermined duration.

Any germs present on the surface to be sampled are thus applied to the nutrient medium and can be detected without an operator having to intervene in the closed or separated area. Contamination of the sterile environment can thus be detected.

In particular, controlled sampling (exact pressure and exact duration of pressing) is made possible by the invention.

It can also be provided that the handling device is designed to grip the contact sample directly during sampling. This represents a particularly simple type of sampling and minimizes the design effort.

Alternatively, it can also be provided that the handling device is designed to feed the contact sample after removal from the contact sample holder, which can be designed e.g., as a magazine, to a sample carrier and to move the sample carrier during sampling. In particular, the sample carrier can be designed to be autoclavable. In contrast to glove ports, which are necessary for manual sampling and which are only decontaminated with hydrogen peroxide (H2O2), autoclaving of the device reduces the risk of contamination of the equipment, the product or falsification of the sample.

The sample carrier has the task of securely holding and retaining the contact sample and simplifying the pressing of the contact sample onto a surface. In particular, the bottom of the contact sample can rest flat on the sample carrier, or the sample carrier can have a corresponding contact surface. In this way, it can be efficiently prevented that the contact sample or its bottom is damaged when it is pressed against the surface to be sampled.

The hold of the contact sample on the contact sample holder can be made by force- or form-locking or by a combination of force- and form-locking. The force fit between the device and the contact sample can be achieved, for example, by a microstructured polymer film or by a vacuum suction cup. Form-locking can be achieved, for example, by means of gripper fingers on the sample carrier. The gripping fingers can be expanded and formed with a recess into which the contact sample can engage.

The fingers can be circumferentially distributed around the contact surface. The contact surface may be covered with the microstructured polymer film just mentioned. The contact surface can comprise a suction opening of the vacuum cup. The connection for a vacuum line can be arranged on a side of the sample carrier opposite the contact surface.

The device may further comprise a lid handling device. The lid handling device may be arranged to remove and/or place the lid of a sample held by the handling device or arranged on the sample carrier. The lid handling device may be designed as a pneumatic cylinder.

It can further be provided that the handling device comprises a gripper with two gripper jaws that can be moved towards and away from each other. In this case, the gripper can be arranged on a gripper member of the handling device that can be pivoted by at least 90°, in particular by 180°, in particular by 360°. This allows the gripper to be used in a particularly flexible manner. The gripper jaws can, in particular, be designed to be complementary to the contact samples (curved, since these are usually circular).

The gripping jaws of the handling device can in particular be designed in such a way that they comprise sections which are complementary to the round shape of the contact samples and/or comprise sections which are complementary to the shape of a grippable section of the sample carrier. The sample carrier and the handling device can also have a coupling device by means of which the sample carrier can be releasably connected to the handling device in a defined position and orientation. This can be realized, for example, by a form-locking rear grip. The sample carrier can comprise a slot-like recess into which a complementary coupling device of the handling device can be introduced, whereby the coupling device of the handling device can engage behind the slot-like recess in the coupled state.

It can be further provided that the contact sample holder comprises a holder for the sample carrier. In this way, the sample carrier is arranged close to the contact sample holder and in a defined position. The handling device can remove a contact sample from the contact sample holder and place it on the sample carrier, in particular on its contact surface. In particular, the contact sample can be held on the contact surface in a force-locking and/or form-locking manner (as described above, for example, by means of a vacuum, microstructured polymer film and/or gripper fingers or other form-locking elements that can grip the contact sample in a form-locking manner). The handling device can then remove the lid of the contact sample. The handling device can then pick up the sample carrier or the contact sample and perform the sampling of the surface.

It is also possible to provide that the contact sample holder is designed to hold several contact samples and that the contact samples can be arranged horizontally in the contact sample holder. In this way, the contact samples are easily accessible and can be used for sampling in a chronologically ordered manner.

It may be further provided that the barrier system comprises a detection device which is designed to detect an identification feature of the contact sample, and in particular to associate the identified contact sample with the time and/or location of a sampling. In this context, it may be further provided that the detection device comprises a barcode reader, an RFID reader, or a DataMatrixCode reader, which is adapted to read a corresponding code on, in, or at a contact sample. Thus, the identification feature may be a barcode or DataMatrixCode, or an RFID feature that is readably attached to, in, or on the contact sample, and the detection device may comprise or be a corresponding reader.

In this way, a specific sampling process (time and location of sampling) can be assigned to a precisely identifiable contact sample via its identification feature. This enables a high degree of traceability and documentability of the sampling.

As mentioned, the contact sample may include an RFID chip. On the RFID chip, the identification feature may be provided. However, the RFID chip may alternatively or additionally comprise other information and/or information may be stored on the RFID chip.

It may further be provided that the detection device is designed to detect the location and/or the time of a sample collection. It may further be provided that the barrier system comprises a data processing system that is configured to assign the location and/or the time of sampling in a data record of a contact sample or its identification feature and, if necessary, to store it and save it in a database.

It may further be provided that the barrier system is configured to be gloveless. The invention makes glove ports superfluous. The glove ports represent weak points in the barrier system. Not using them increases the reliability of the barrier system.

As already stated above, the present invention also relates to a method for automated sampling in a closed or separated area of a barrier system. The barrier system is in particular an isolator of a production plant, which is in particular a pharmaceutical production plant. A sterile environment is provided in the closed or separated area. The method can be used to reliably monitor, document and ensure the quality of the sterile environment.

At least one handling device is arranged in the closed or separated area. Further, a contact sample is provided in the closed or separated area.

Within the scope of the method according to the invention, the handling device grasps the provided contact sample. The handling device opens the contact sample. The handling device thus carries out a work step in which the lid of the contact sample is removed so that the nutrient medium of the contact sample is accessible. The handling device automatically performs sampling on a surface section in the closed or separated area using the opened contact sample. During the sampling process, the contact sample or its nutrient medium is brought into contact with the surface to be sampled. The sampling is performed in a reproducible manner. The sampling parameters are therefore repeatable. A second sampling can be performed with the same parameters.

According to the invention, it is provided in particular that after a first production interval, a first sampling is carried out by means of the method just described or the later described embodiments or the alternative method with two handling devices. This first sampling is carried out with first sampling parameters. After a second production interval, a second sampling is performed by means of the method just described or the later described embodiments or the alternative method with two handling devices. This first sampling is performed with second sampling parameters. The first and second sampling parameters may comprise at least one preferably more identical sampling parameters, preferably the sampling parameters are all identical. The sampling parameters may comprise one or more of the following: sample contact pressure, sample contact duration, sampling location.

According to the invention, it can be provided for carrying out the method that the handling device places the contact sample on a sample carrier after it has been grasped. The sample carrier holds the contact sample, in particular, in a force-locking and/or form-locking manner. After placing on the sample carrier, the handling device opens the contact sample. For sampling, the handling device can grip the sample carrier and move the sample carrier with the contact sample held on it to the surface section to be sampled in the closed or separated area and carry out the sampling. For this purpose, the contact sample or its nutrient medium is brought into contact with the surface to be sampled. The sample carrier with the contact sample placed on it is moved by means of the handling device.

It is also possible for the handling device to orient the contact sample or the sample carrier with the contact sample held on it during sampling in such a way that a sample surface of the contact sample is aligned parallel to the surface of the sampled surface section. The contact sample can then be pressed against it, in particular with defined pressure and/or for a defined duration, by a translatory movement. The parallel orientation makes the movement for pressing on particularly simple.

It is also possible for the handling device to reseal the contact sample after sampling. For this purpose, the handling device can set down the contact sample or the sample carrier with the contact sample held on it and put on the lid. If necessary, the handling device can pick up the contact sample or the sample carrier with the contact sample held on it again and feed it to a further work step. For example, the contact sample can be fed to a storage area for the sample or to an airlock to be removed from the closed or separated area.

It can be further provided that the handling device feeds the contact sample to a detection device before or after taking the sample. The detection device detects an identification feature of the contact sample. The identification feature can then be associated with a sampling, in particular its time and/or location. The identification feature may be a bar code or a data matrix code (the contact sample may also include an RFID chip that provides the identification feature in a readable manner). The detection device may be or include a camera and/or a bar code and/or data matrix code reader or RFID reader. In particular, the identification feature may be stored in a data processing system together with data characterizing the sampling, in particular its time and/or location (sampling location in the closed or separated area). For example, the identification feature can be stored in a table together with the data characterizing the sampling. This favors an automated recording of the individual samplings.

It can further be provided that the handling device removes the contact sample from a contact sample holder before sampling and/or supplies it to a contact sample holder after sampling. The contact sample holder can be of shelf-like design with compartments or holders for a plurality of contact samples. For example, the contact sample holder may be insertable or removable into the closed or separated area via an airlock with the samples therein. For this purpose, the contact sample holder can be detachably fixed in the closed or separated area.

As stated above, the present invention also relates to a method for automated sampling in a closed or separated area of a barrier system, wherein at least two handling devices are arranged in the closed or separated area. The barrier system may be an isolator. The barrier system is part of a production plant, in particular a pharmaceutical production plant. The closed area provides a sterile environment. In the closed or separated area, a contact sample is provided. The further embodiments already mentioned with respect to the method with one handling device and with respect to the barrier system are also to be understood as further embodiments of the method with at least two handling devices.

The method includes the steps:

One of the handling devices grasps the provided contact sample. One of the handling devices opens the provided contact sample. One of the handling devices performs a sampling on a surface section in the closed or separated area with the contact sample. The method optionally comprises one or more of the following steps. Closing the contact sample after sampling. Placing the contact sample after the grasp on a sample carrier that holds the contact sample, in particular in a force-locking and/or form-locking manner. Gripping the sample carrier for sampling and moving the sample carrier with the contact sample held on it to a surface section in the closed or separated area and subsequently carrying out the sampling. In this regard, the method provides that each of the handling devices performs at least one of the steps of the method. For example, it may be envisaged that a first handling device removes the contact sample from a contact sample holder while a second handling device receives the sample carrier, the first handling device places the contact sample on the sample carrier and removes the lid. The second handling device then performs the sampling with the sample held by the sample carrier. After sampling, the first handling device can put the lid back on and remove the contact sample from the sample carrier and return it to the contact sample holder or to an airlock of the barrier system.

The advantage of using two handling devices to divide up the work is that operations can be carried out more quickly and the radius of action of the handling devices is greater than with a single handling device.

In particular, it is in the scope of the present invention that the detection area of the detection device covers the radius of action of the handling device, or that the handling device can feed a contact sample to the detection area of the detection device. The documentation of the sampling is advantageous, as this allows the state of the closed or separated area to be safely and reliably logged.

The handling device can always press the contact sample onto the surface with the same force, either force-controlled by means of a force sensor, for example, or displacement-controlled, for example with the aid of a resilient element. The reproducibility of the sampling can thus be increased even further.

The force sensor or the resilient element can be arranged in the handling device or in the sample carrier. Also in the scope of the invention is a combination of force and displacement control. The data generated in this process, such as contact force and time, can also be used for documentation.

Pressing on the contact sample with a defined force can help to prevent the nutrient medium, e.g. the agar, from falling out of the sample. This occasionally occurs during manual sampling by operators and disturbs the production process or sampling, which usually takes place after production.

In the scope of the present invention, it is also particularly envisaged that handling device can sample several sampling locations arranged differently in the closed or separated area.

The detection device or a further monitoring device can be provided and designed to check whether the nutrient medium is still present in the contact sample after the sample has been taken. The monitoring device may be designed as a camera system, for example. If the absence of the nutrient medium in the sample is detected, the sampling can be repeated, for example, at a predefined additional location.

According to the invention, it is particularly intended that after a first production interval, a first sampling is carried out by means of one of the methods just described (method with one handling device or method with 2 handling devices). This first sampling is carried out with first sampling parameters. Sampling parameters are the parameters that characterize the sampling. On the basis of the sampling parameters, the way of sampling can be traced. After a second production interval, a second sampling is performed using one of the methods just described (method with one handling device or method with 2 handling devices). This second sampling is performed with second sampling parameters. The first and second sampling parameters thereby comprise at least one preferably several identical sampling parameters, preferably the sampling parameters are all identical. The sampling parameters may include one or more of the following: sample contact pressure, sample contact duration, sampling location.

The first production interval and the second production interval can in particular be of equal length. The first and second sampling can in particular take place after the same length of operation.

In particular, the sampling parameters can be stored on and read from an RFID chip of the respective contact sample used.

BRIEF DESCRIPTION OF THE FIGURES

The invention is explained in more detail below with reference to the accompanying figures. They show.

DETAILED DESCRIPTION

Figure 1:
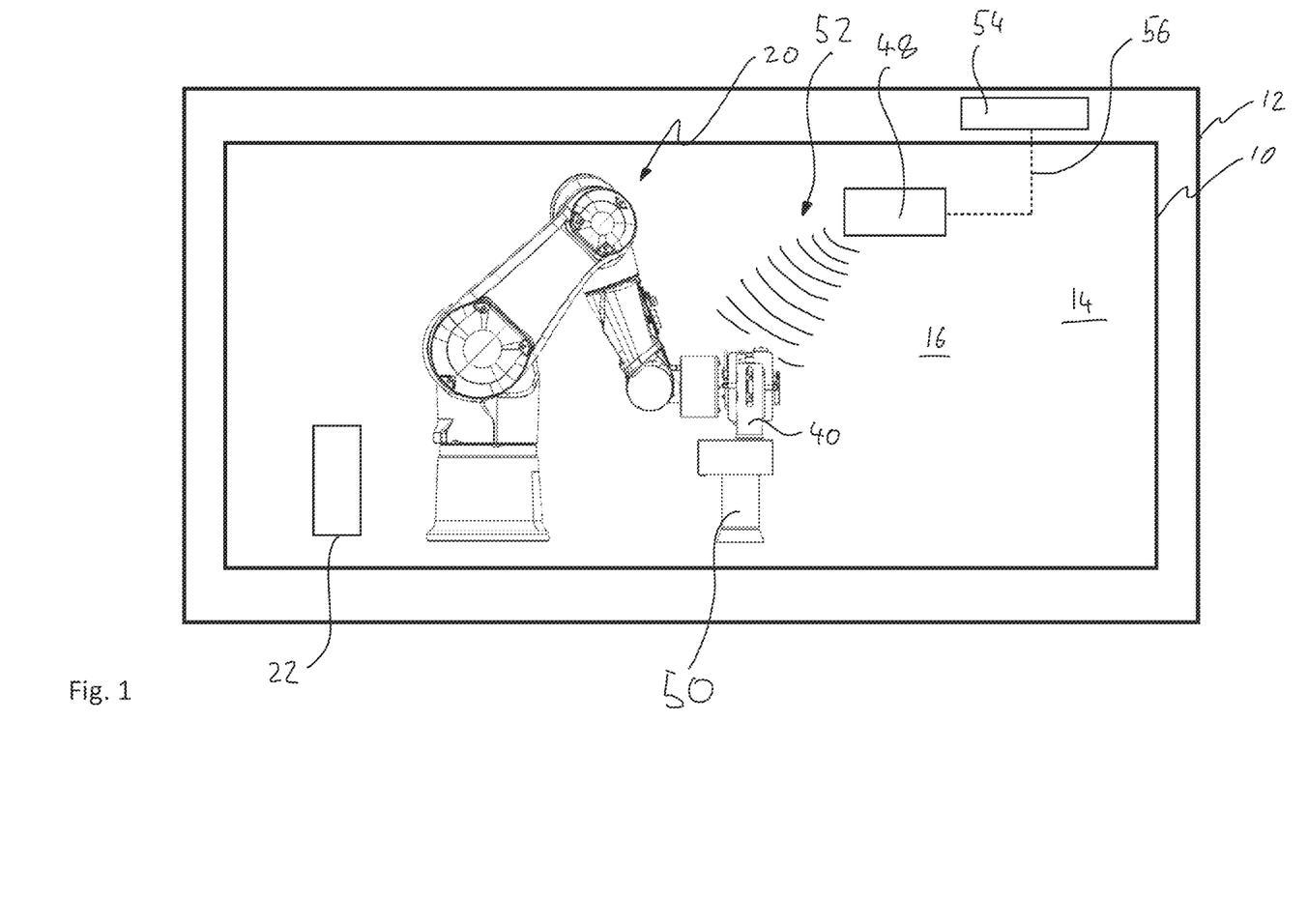
FIG. 1 a schematically illustrated production plant with a closed or separated area.

FIG. 1 shows a pharmaceutical production plant 12 with a barrier system 10 comprising a closed or separated area 14. The barrier system 10 is designed as an isolator 10. A sterile environment 16 is provided in the closed or separated area 14 of the isolator 10.

Figure 2:
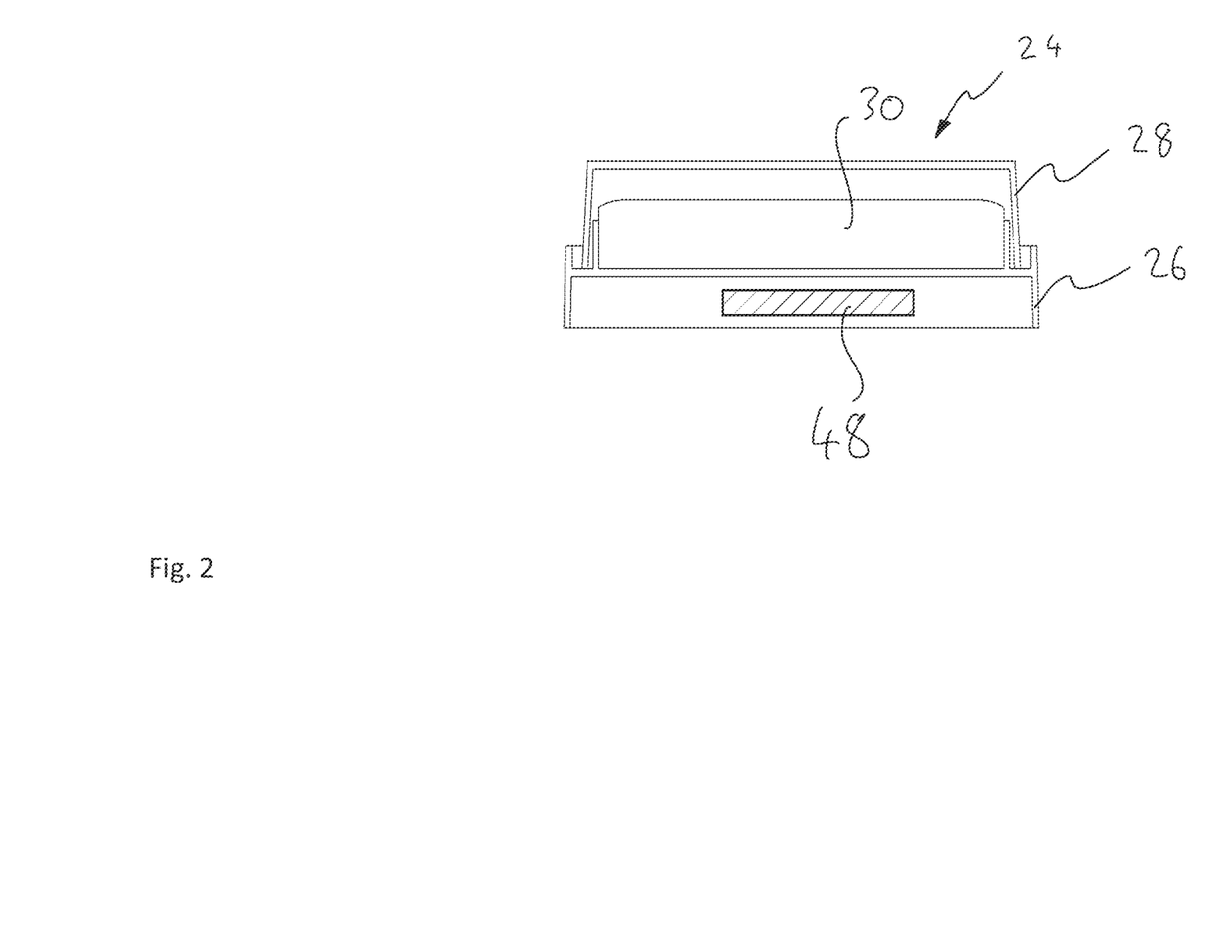
FIG. 2 a contact sample in a sectional view.

Within the enclosed or separated area 14 is a handling device 20 and a contact sample holder 22. The contact sample holder 22 is configured to provide at least one contact sample 24 as illustrated in FIG. 2. In the present embodiment, the shown contact sample holder 22 is configured to receive a plurality of contact samples 24, and the contact samples 24 are horizontally arrangeable in the contact sample holder 22. As shown in detail in FIG. 2, the contact sample 24 includes a bottom 26 and a lid 28. A nutrient medium 30, typically agar, is disposed on the bottom 26 and closed by the lid 28. An identification feature 48 is further disposed on the bottom 26, which may be, for example, a QR code (data matrix code, or bar code, or information in a RFID chip). The identification feature 48 is typically located on the outer jacket surface of the bottom 26. The lid 28 is removable so as to expose a sample surface 31 of the contact sample 24 or nutrient medium 30.

The handling device 20 is configured to remove the provided contact sample 24 from the contact sample holder 22, to open it and to perform a sampling on a surface section 42 in the closed or separated area 14. The surface section 42 to be sampled is thereby arranged on a sample location 50, which is configured to enable reproducible sampling.

Figure 3:
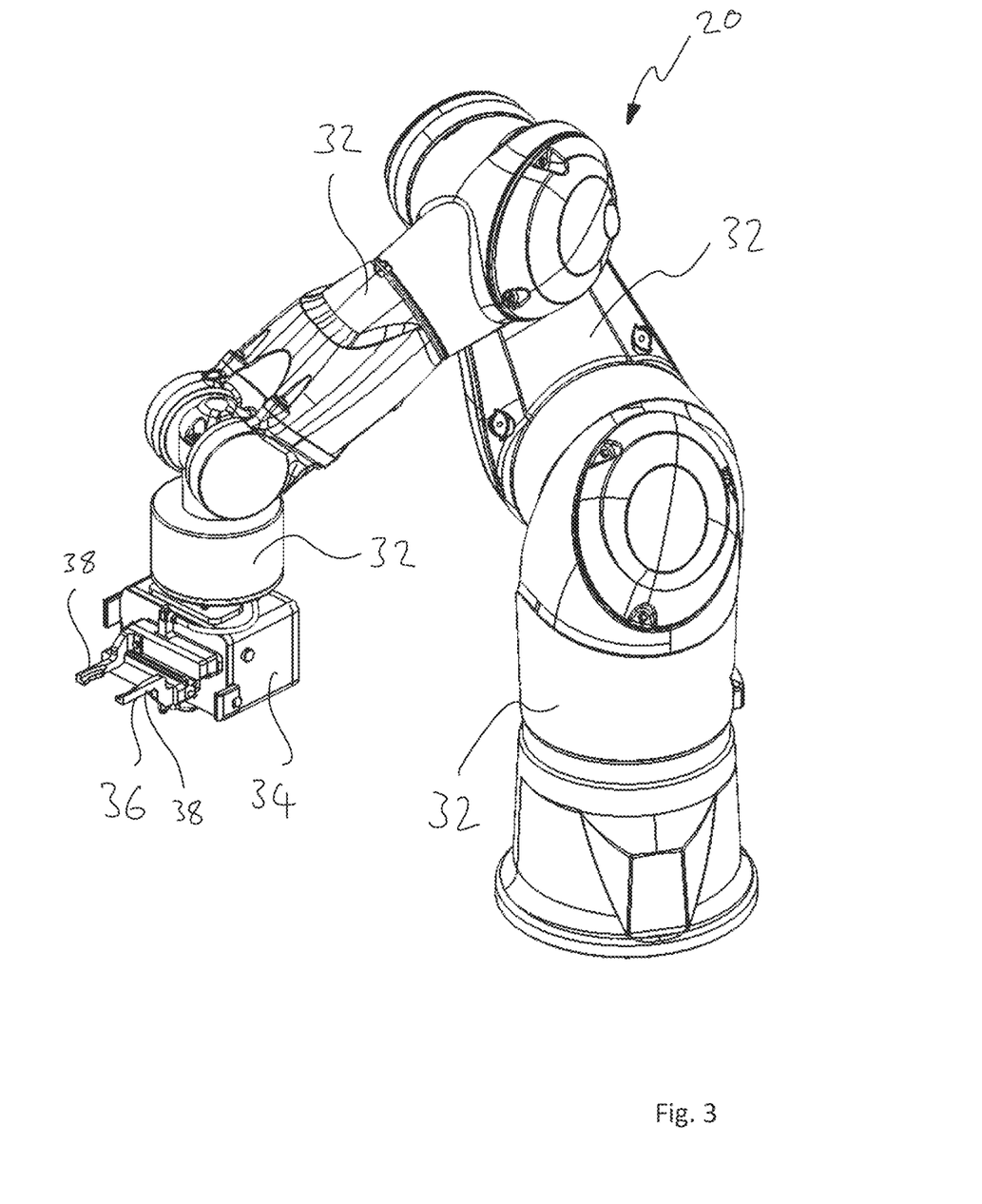
FIG. 3 a handling device in a perspective view.
Figure 4:
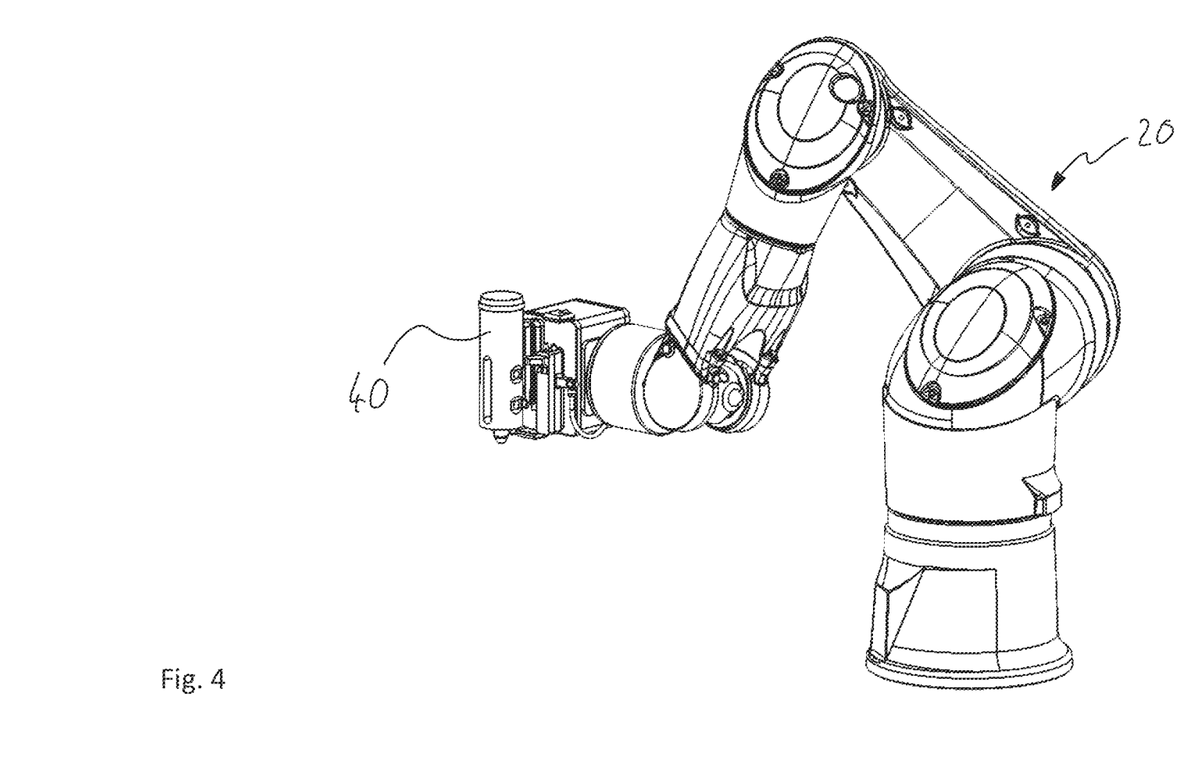
FIG. 4 another perspective view of the handling device with a sample carrier.

The handling device 20 is designed to be able to directly grip the contact sample 24 during sampling. For this purpose, the handling device 20 has a gripper 36 with gripper jaws 38, as can be seen clearly in FIG. 3. The gripper 36 is arranged on a 3600 pivotable gripper member 34 of the handling device 20. The handling device 20 has a plurality of pivotally interconnected members 32 to allow the gripper to move freely in space.

Figure 5:
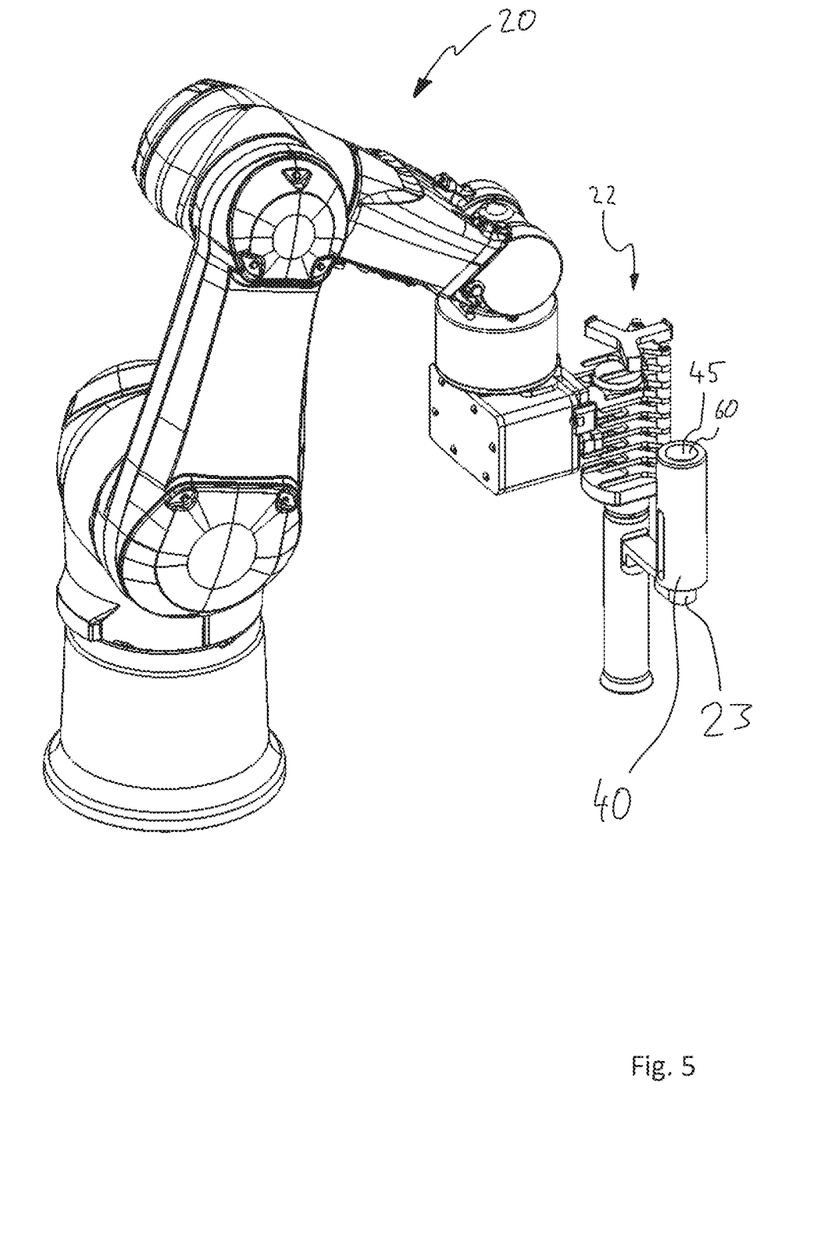
FIG. 5 the handling device with a contact sample holder in a further perspective view.

As shown in FIG. 5, the contact sample holder 22 may include a holder 23 for a sample carrier 40. Although the handling device 20 can directly grasp the contact sample 24 via the gripper 36, it can also use the sample carrier 40 for sampling.

Figure 6:
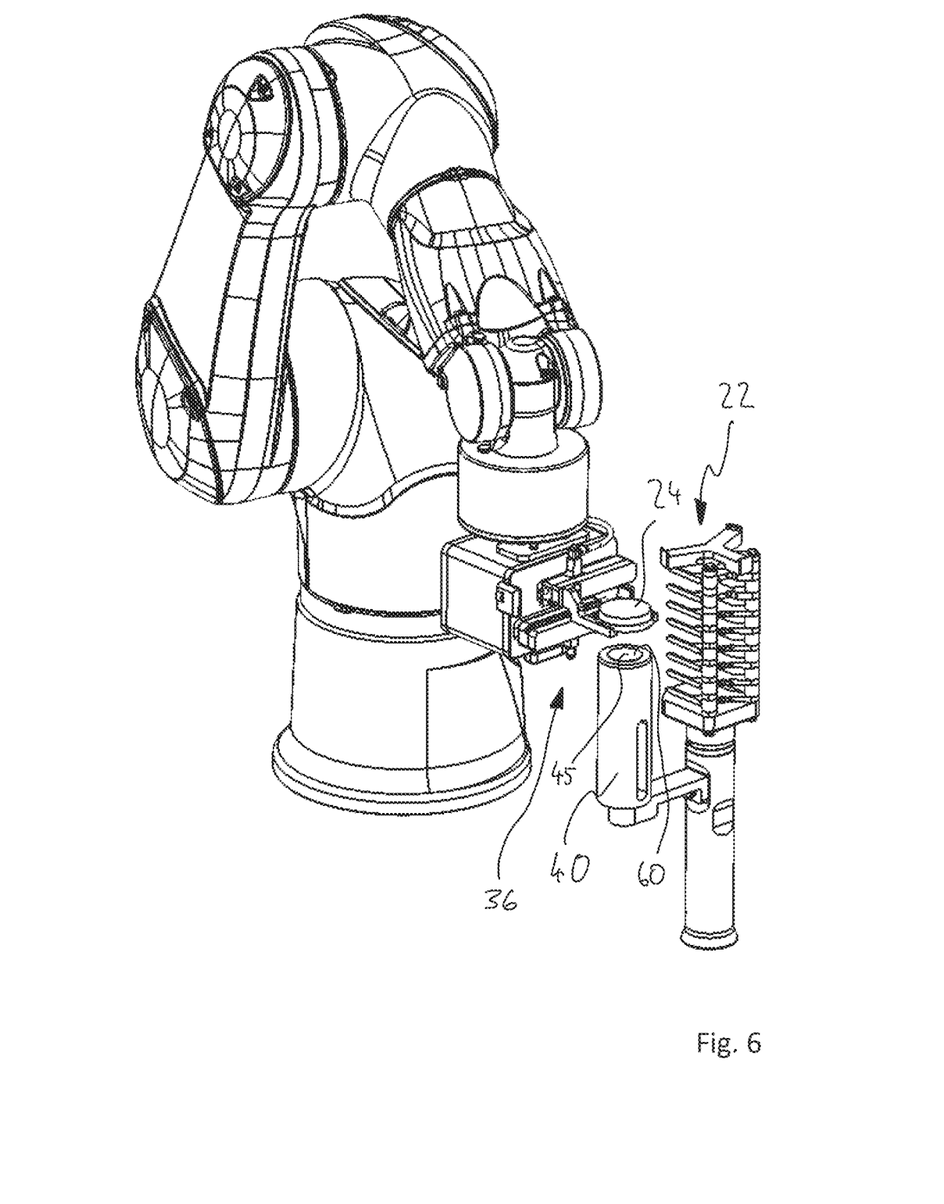
FIG. 6 the handling device in a further perspective view.
Figure 7:
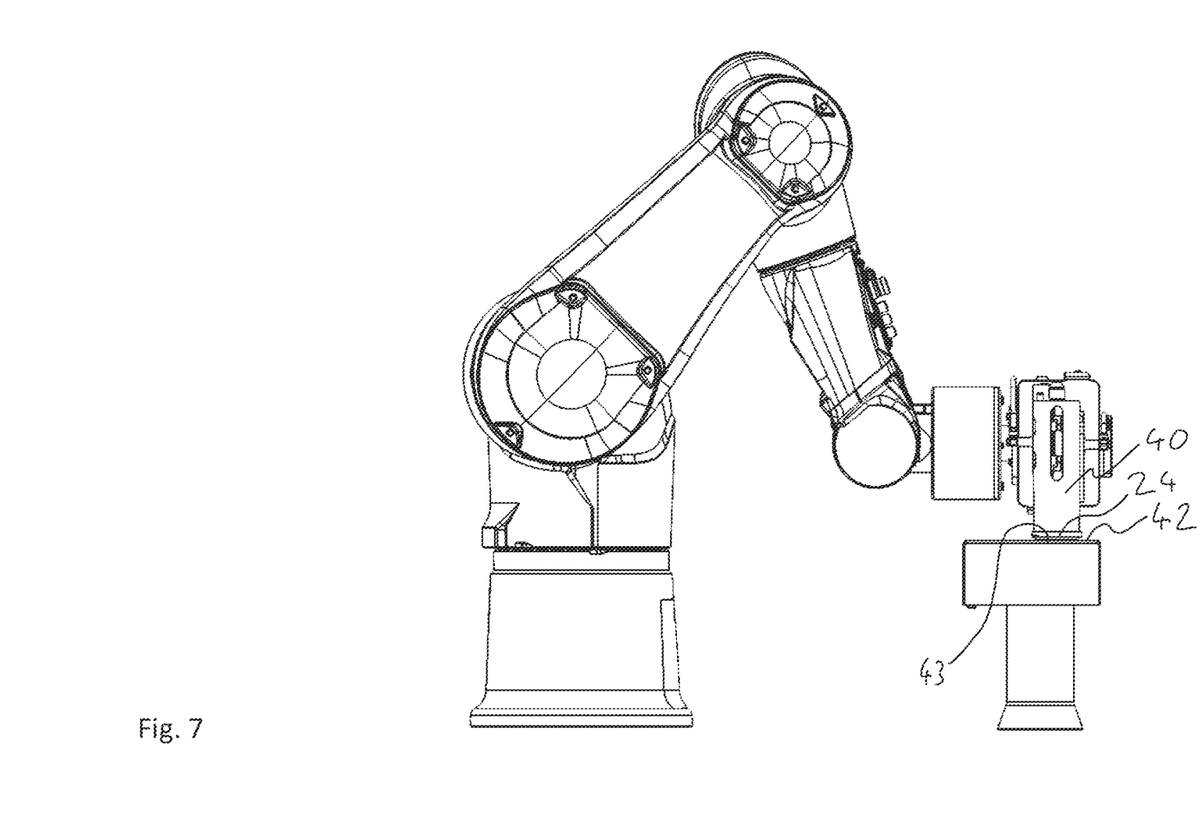
FIG. 7 a side view of the handling device during sampling.
Figure 8:
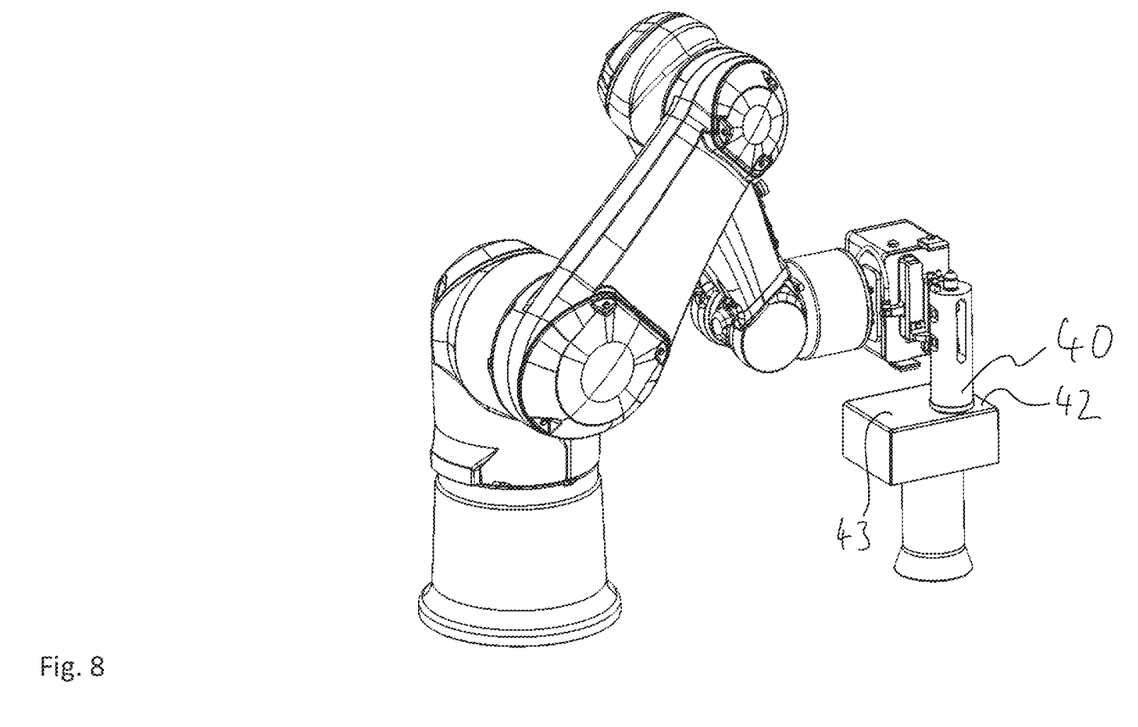
FIG. 8 a perspective view of the handling device during sampling.

The handling device 20 is appropriately configured to feed the contact sample 24 to the sample carrier 40 after removal from the contact sample holder 22 (see FIGS. 5 and 6), and to move the sample carrier 40 during sampling (see FIGS. 7 and 8). The sample carrier will be explained in further detail below.

The barrier system 10 includes a detection device 46 configured to detect an identification feature 48 of the contact sample 24. The detection device 46 typically includes or is a bar code reader or a DataMatrixCode reader. Accordingly, the identification feature 48 may be a corresponding code (bar code or DataMatrixCode) on a contact sample 24. The contact sample 24 may also include a RFID chip having the identification feature 48, such that the identification feature 48 is provided as information on the RFID chip in a readable manner.

The detection device 46 is connected to a data processing system 54 via a data link 56, which may be wired or wireless. The data processing system 54 may associate the identified contact sample 24 (recognized by its identification feature 48) with the time and/or location of a respective sampling, for example, storing it as a corresponding data record. The detection area 52 of the detection device 46 may include the range of movement of the handling device 20, or the contact sample 24 may be moved into the detection area 52 of the detection device 46 with its identification feature 48.

Since the steps required for sampling are automated in the production plant 12, the barrier system 10 can be designed to be glove-port-free.

According to the invention, there is also a method for automated sampling in the closed or separated area 14 of the barrier system 10. Here, as in the production plant 12 according to the invention, at least one handling device 20 is arranged in the closed or separated area 14. In the closed or separated area 14, the method involves providing the contact sample 24, and the handling device 20 grasps (FIG. 6) the provided contact sample 24, opens it by removing the lid 28 of the contact sample 24, and performs a sampling on a surface portion 42 in the closed or separated area 14.

In FIG. 7, the sampling is shown, whereby the contact sample 24 has been placed on the sample carrier 40 by means of the handling device 20.

Figure 9:
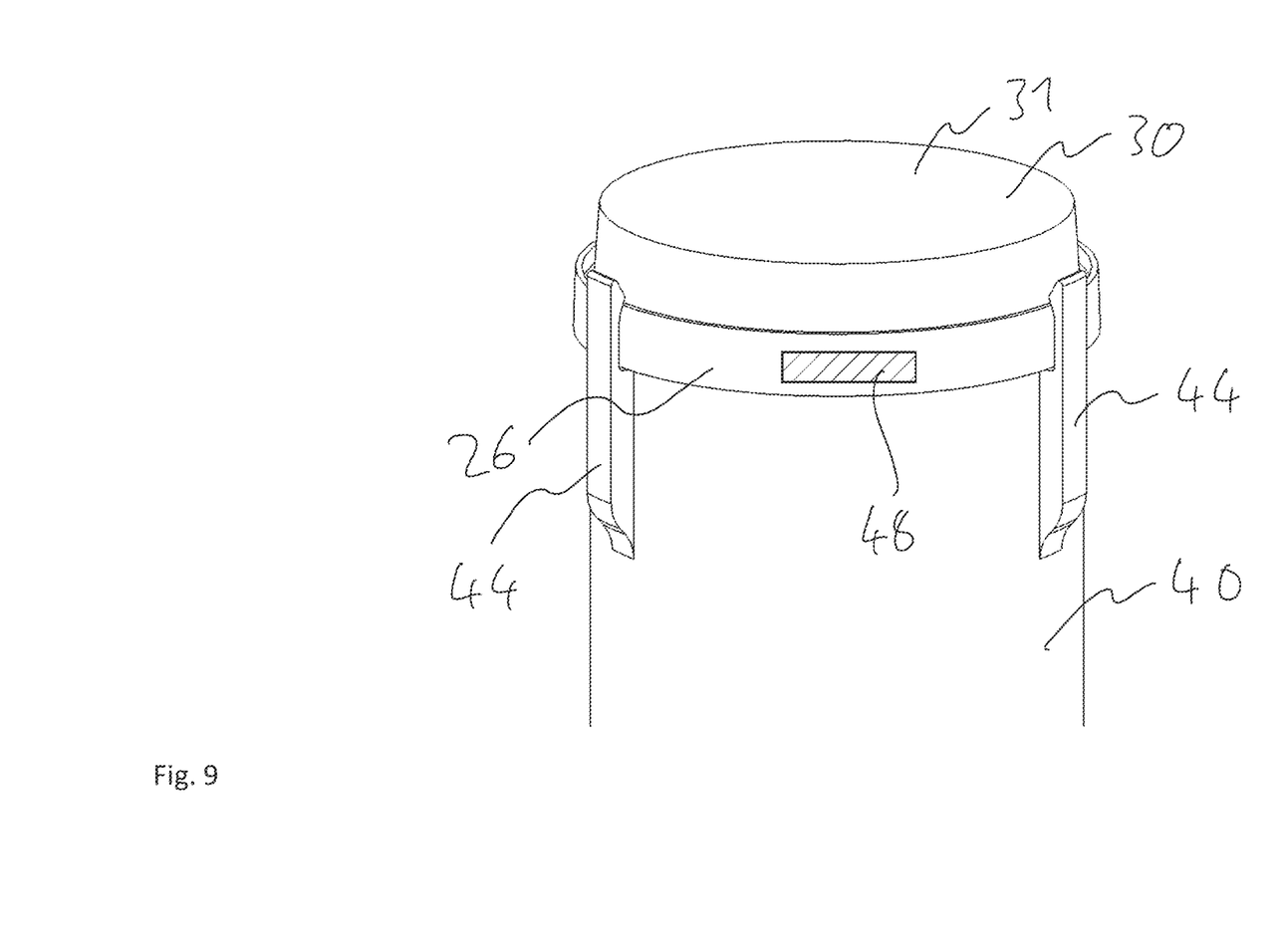
FIG. 9 a contact sample on a sample carrier.
Figure 10:
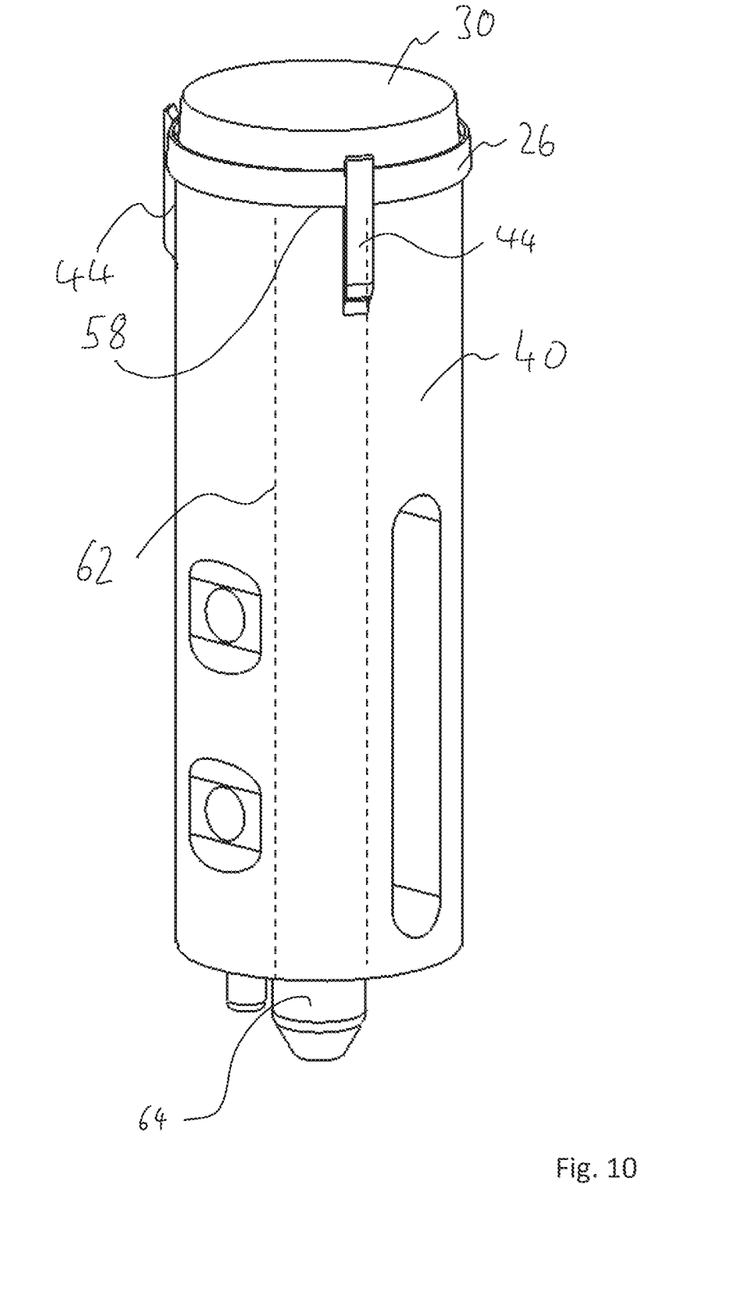
FIG. 10 a sample carrier with a contact sample.

The sample carrier 40 holds the contact sample 24 in a force-locking (variant FIGS. 4 to 8) and/or form-locking (variant FIGS. 9 and 10) manner. The form-locking is achieved via several fastening fingers 44, which are shown in FIGS. 9 and 10. The fastening fingers 44 are arranged evenly distributed in the circumferential direction around a contact surface 45. The contact surface 45 is designed in such a way that the contact sample 24 can be placed flat thereon. The contact sample 24 can be held in a force-locking manner via a suction opening 58 or an adhesive surface 60, which can be formed, for example, as a microstructured polymer film. The suction opening 58 is connected to a connection 64 for a vacuum supply via a pressure line that runs in the sample carrier 40.

The handling device 20 opens the contact sample 24, which is held on the sample carrier 40. For sampling, it grasps the sample carrier 40 and moves the sample carrier 40 with the contact sample 24 held on it to the surface section 42 in the closed or separated area 14 and performs sampling by pressing the nutrient medium against a surface 43 of the sampled surface section 42.

During the sampling, the handling device 20 orients the contact sample 24 or the sample carrier 40 with the contact sample 24 held on it in such a way that a sample surface 31 of the contact sample 24 is aligned parallel to the surface 43 of the sampled surface section 42 and is pressed against it, in particular with defined pressure and for a defined duration.

After the sampling, the handling device 20 reseals the contact sample 24 by placing the lid on it.

The handling device 20 feeds the contact sample 24 to the detection device 46 before or after sampling, and the detection device 46 detects the identification feature 48 (see FIG. 9) of the contact sample 24. After sampling and detection of the identification feature 48, the handling device 20 feeds the contact sample 24 back to the contact sample holder 22.

Figure 11:
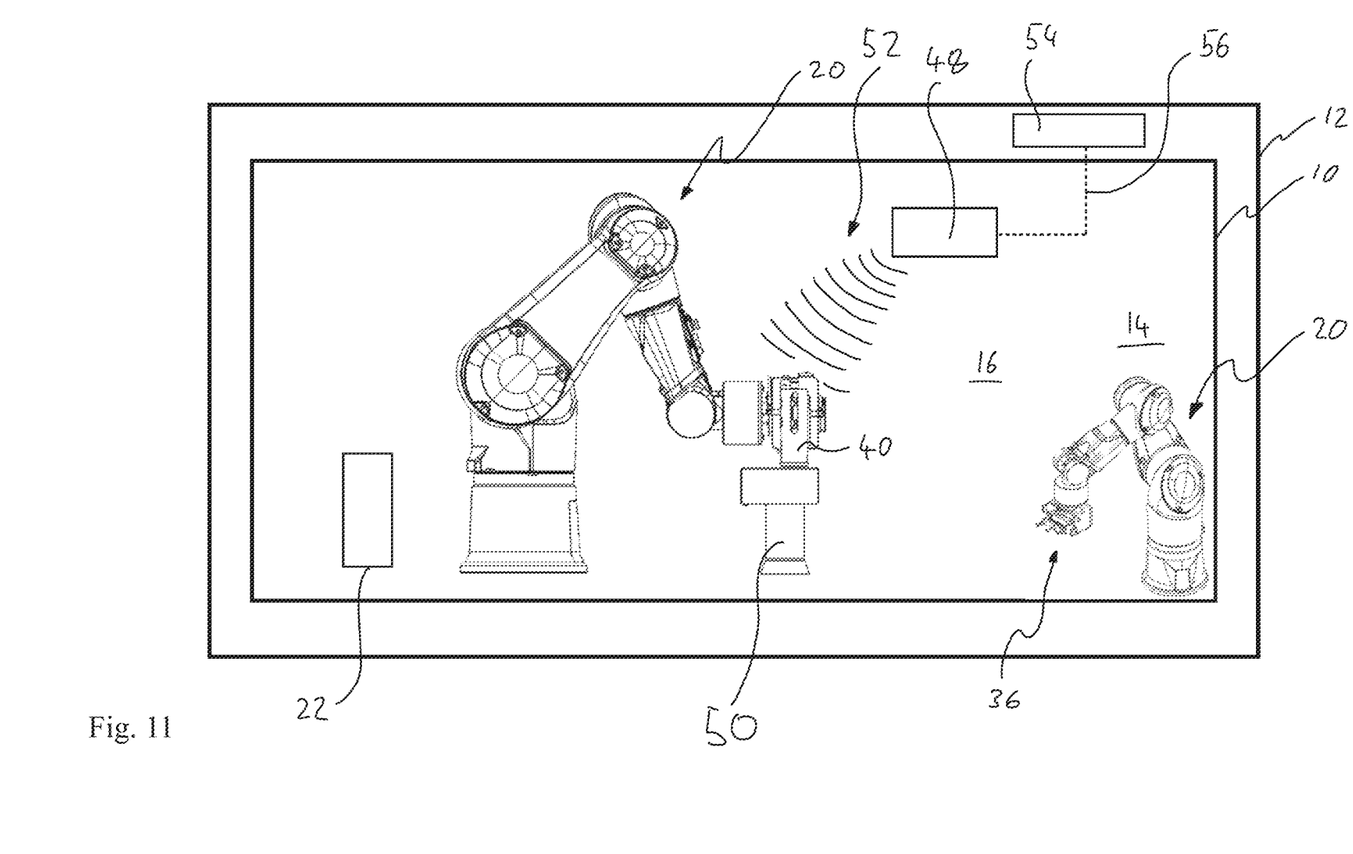
FIG. 11 a schematically illustrated production plant with a closed or separate area in which two handling devices are arranged that can carry out sampling based on the division of work.

FIG. 11 illustrates a barrier system 10 with two handling devices 20. The handling devices 20 operate alternately and perform different steps required for sampling. The first of the two handling devices 20 grasps the provided contact sample 24. The second of the two handling devices 20 opens the provided contact sample 24, i.e. removes its lid 28 the first handling device 20 places the contact sample 24 on a sample carrier 40, the second handling device 20 grips the sample carrier 40 and performs sampling with the contact sample 24 on the surface section 42 in the closed or separated area 14. After sampling, the first handling device 20 reseals the contact sample 24 by placing the lid 28 on it. Thereafter, the second handling device 20 places the contact sample 24 back into the contact sample holder 22. The individual steps can also be performed by the respective other handling device 20, but each of the handling devices 20 performs at least one of the steps of the method. This relates to the process variant according to the invention with two handling devices.

What is claimed is:

1. A barrier system (10) of a production plant (12), the barrier system (10) having a closed or separated area (14) in which a sterile environment (16) is provided, wherein the barrier system (10) comprises:
   in the closed or separated area (14), a handling device (20) and a contact sample holder (22) are arranged,
   wherein the contact sample holder (22) is configured to provide at least one contact sample (24), and wherein the handling device (20) is configured to automatically remove the contact sample (24) from the contact sample holder (22), open the contact sample (24), and automatically perform sampling of the contact sample (24) on a surface section (42) in the closed or separated area (14) in a reproducible manner.

2. The barrier system (10) according to claim 1, wherein the handling device (20) is configured to directly grip said contact sample (24) during sampling.

3. The barrier system (10) according to claim 1, wherein the handling device (20) is configured to feed the contact sample (24) to a sample carrier (40) after removal and to move the sample carrier (40) during sampling.

4. The barrier system (10) according to claim 3, wherein the contact sample holder (22) comprises a holder (23) for the sample carrier (40).

5. The barrier system (10) according to claim 1, wherein the handling device (20) comprises a gripper (36) with two gripper jaws (38) which are movable towards and away from each other, and wherein the gripper (36) is arranged on a gripper member (34) of the handling device (20) which is pivotable by at least 90°.

6. The barrier system (10) according to claim 1, wherein the contact sample holder (22) is configured to receive a plurality of contact samples (24) arranged horizontally in the contact sample holder (22).

7. The barrier system (10) according to claim 1, wherein the barrier system (10) further comprises a detection device (46) configured to detect an identification feature (48) of the contact sample (24).

8. The barrier system (10) according to claim 7, wherein the detection device (46) comprises one selected from the group consisting of a bar code reader, a DataMatrixCode reader, a plain text code reader and a RFID reader, which is configured to read a corresponding code or an information on a contact sample (24) or a data carrier, on the contact sample (24).

9. The barrier system (10) according to claim 7, wherein the detection device (46) is configured to detect a location and/or a time of a sample extraction of the contact sample (24).

10. The barrier system (10) according to claim 9, wherein the barrier system (10) comprises a data processing system (54) which is configured to associate the location and/or the time of the sample extraction in a data record with the identification feature (48) of the contact sample (24).

11. The barrier system (10) according to claim 1, wherein the barrier system (10) is glove-port-free.

12. A method for automated sampling in a closed or separated area (14) of a barrier system (10), wherein a sterile environment (16) is provided in the closed or separated area (14), wherein the method comprises:
arranging at least one handling device (20) in the closed or separated area (14),
providing a contact sample (24) in the closed or separated area (14), and
grasping, with the handling device (20), the provided contact sample (24), opening it and carrying out sampling on a surface section (42), which is arranged in the closed or separated area (14).

13. The method according to claim 12, wherein the handling device (20), after the grasp, places the contact sample (24) on a sample carrier (40), opens the contact sample (24), and, for sampling, grips the sample carrier (40) and moves the sample carrier (40) with the contact sample (24) held thereon to a surface section (42) in the closed or separated area (14) and carries out the sampling.

14. The method according to claim 12, wherein during sampling the handling device (20) orients the contact sample (24) or the sample carrier (40) with the contact sample (24) held thereon in such a way that a sample surface (31) of the contact sample (24) is aligned parallel to, and is pressed against, a surface (43) of the surface section (42).

15. The method according to claim 12, wherein the handling device (20) closes the contact sample (24) after sampling.

16. The method according to claim 12, wherein the handling device (20) feeds the contact sample (24) to a detection device (46) before or after sampling, and the detection device (46) detects an identification feature of the contact sample (24) and assigns the identification feature (48) to a sampling.

17. The method according to claim 12, wherein at least one contact sample holder (22) is provided for holding the contact sample (24), and the handling device (20) performs at least one selected from the group consisting of removing the contact sample (24) from the contact sample holder (22) before sampling, and feeding the contact sample (24) to the contact sample holder (22) after sampling.

18. The method according to claim 12, wherein, after a first production interval a first sampling is performed with first sampling parameters and that after a second production interval a second sampling is performed with second sampling parameters, and wherein the first and second sampling parameters comprise at least one identical sampling parameter.

19. The method according to claim 18, wherein the first and second sampling parameters comprise one or more of the following parameters: sample contact pressure, sample contact duration, and sampling location.

20. A method for automated sampling in a closed or separated area (14) of a barrier system (10) of a production plant (12), wherein a sterile environment (16) is provided in the closed or separated area (14), wherein
at least two handling devices (20) are arranged in the closed or separated area (14), and
a contact sample (24) is provided in the closed or separated area, and
wherein the method comprises the following steps:
one of the handling devices (20) grasps the provided contact sample (24),
one of the handling devices (20) opens the provided contact sample (24),
one of the handling devices (20) performs sampling with the contact sample (24) on a surface portion (42) in the closed or separated area (14), and
wherein each of the handling devices (20) carries out at least one of the steps of the method.

21. The method according to claim 20, wherein the method comprises one or more of the following steps:
closing the contact sample (24) after the sampling,
placing the contact sample (24) after the grasp on a sample carrier (40) which holds the contact sample (24), in particular in a force-locking and/or form-locking manner, and
gripping the sample carrier (40) for sampling and moving the sample carrier (40) with the contact sample (24) held thereon to a surface section (42) in the closed or separated area (14) and subsequently carrying out the sampling.

* * * * *